United States Patent [19]

Chiddix

[11] 4,371,723

[45] Feb. 1, 1983

[54] PROCESS OF PRODUCING A DISTILLED BUTANEDIOL PRODUCT OF HIGH QUALITY IN HIGH YIELD

[75] Inventor: Max E. Chiddix, League City, Tex.

[73] Assignee: GAF Corporation, New York, N.Y.

[21] Appl. No.: 290,548

[22] Filed: Aug. 6, 1981

Related U.S. Application Data

[63] Continuation of Ser. No. 140,926, Apr. 16, 1980, abandoned, which is a continuation of Ser. No. 812,615, Jul. 5, 1977, abandoned, which is a continuation-in-part of Ser. No. 675,686, Apr. 9, 1976, abandoned.

[51] Int. Cl.³ ............................................. C07C 31/20
[52] U.S. Cl. ...................................... 568/861; 568/856
[58] Field of Search .............................. 568/861, 856

[56] References Cited

U.S. PATENT DOCUMENTS

| 2,463,677 | 3/1949 | Brandner | 568/872 |
| 2,628,986 | 2/1953 | Wallace et al. | 568/917 |
| 2,775,621 | 12/1956 | Maclean et al. | 568/824 |
| 3,040,104 | 6/1962 | Sarappo et al. | 568/872 |
| 3,479,411 | 11/1969 | Adam et al. | 568/861 |
| 3,784,408 | 1/1974 | Jaffe et al. | 568/863 |
| 3,985,815 | 10/1976 | Jaffe et al. | 568/868 |
| 4,001,344 | 1/1977 | Hoffmann et al. | 568/857 |

FOREIGN PATENT DOCUMENTS

| 877643 | 9/1961 | United Kingdom . | |
| 282306 | 12/1970 | U.S.S.R. | 568/861 |

Primary Examiner—Joseph E. Evans
Attorney, Agent, or Firm—James Magee, Jr.; Marilyn J. Maue

[57] ABSTRACT

In accordance with the present invention, there is provided herein a process for producing a distilled butanediol product of high quality in high yield. The process begins with a crude butynediol solution which is made by an ethynylation reaction between aqueous formaldehyde and acetylene. The crude butynediol solution contains at least a metallic ion, usually sodium, magnesium and/or calcium ion, and an anion, particularly, formate ion, and usually also acetate ion, and often silicic acids and silicic acid salts, as impurities, and unreacted formaldehyde. After substantially stripping the solution of the unreacted formaldehyde, the stripped solution is treated with ion exchange resin, including at least a cation exchange resin to remove one or more of the metallic ions present, and as an anion exchange resin to remove the formate ion, and the acetate ion and silicic acids and silicic acid salts, should they be present in the solution. The deionized butynediol solution then is hydrogenated to form a purified butanediol solution, which is fractionally distilled while maintaining the residue thereof in a fluid state to provide a butanediol product of high quality in high yield.

15 Claims, 2 Drawing Figures

PROCESS OF PRODUCING A DISTILLED BUTANEDIOL PRODUCT OF HIGH QUALITY IN HIGH YIELD

This application is a continuation of Ser. No. 140,926, filed Apr. 16, 1980 which is a continuation of Ser. No. 812,615, filed July 5, 1977 which is a continuation-in-part of Ser. No. 675,686, filed Apr. 9, 1976, all abandoned.

BACKGROUND OF THE INVENTION

1. Field of the Invention

This invention relates to the production of butanediol, and, more particularly, to a process of producing a distilled butanediol product of high quality in high yield.

2. Description of the Prior Art

Butanediol is prepared by catalytic hydrogenation of butynediol, as described in U.S. Pat. No. 3,449,445. The butynediol is obtained by a catalytic ethynylation reaction between aqueous formaldehyde and acetylene, which is described, for example, in U.S. Pat. Nos. 2,871,273, 2,939,844, 3,108,140, 3,294,849, 3,560,576, 3,723,545 and 3,920,759.

The butynediol solutions that are produced by ethynylation, however, contain a number of impurities, including dissolved salts, such as sodium formate, calcium formate, magnesium formate and sodium acetate; silicic acids and silicic acid salts, and some unreacted formaldehyde. These impurities arise in a variety of ways. The formates always are present as a result of the Canizzaro reaction of the formaldehyde reactant with itself. Sodium acetate results when it is used as a buffer to control the pH of the reaction medium during ethynylation. Calcium and magnesium ions, and silicic acids and silicic acid salts, are leached out of the ethylation catalyst.

These aforementioned salts, particularly the formates and acetates, interfere with the final distillation step of producing the butanediol product, and the other impurities, such as the metallic ions, the silicic acids and silicic acid salts, and the excess formaldehyde, reduce the lifetime of the hydrogenation catalyst used to convert the butynediol to butanediol.

In particular, it has been found now that during this final fractional distillation of the butanediol product from the crude butanediol solution, the residue of the distillation forms a gel, even at high temperatures, thus trapping part of the butanediol and reducing the yield thereof. This highly undesirable result is compounded by the fact that the gelled residue containing butanediol does not flow and cannot be pumped. Accordingly, it has been necessary, in the past, whether in a batch or continuous process, to leave a considerable amount of butanediol liquid with the gelled residue to keep it fluid and pumpable, thus contributing further to loss of yield of product. In actual plant operation, at least 5% of the butanediol liquid must be left in the residue to insure a fluid condition.

Prior to this invention, there was no satisfactory means by which to resolve the problems of loss of yield by gel formation, and loss of activity and lifetime of the hydrogenation catalyst.

SUMMARY OF THE INVENTION

In accordance with the present invention, there is provided herein a process for producing a distilled butanediol product of high quality in high yield. The process begins with a crude butynediol solution which is made by an ethynylation reaction between aqueous formaldehyde and acetylene. The crude butynediol solutions contains at least a metallic ion, usually sodium, magnesium and/or calcium ion, and an anion, particularly, formate ion, and usually also acetate ion, and often silicic acids and silicic acid salts, as impurities, and unreacted formaldehyde. After substantially stripping the solution of the unreacted formaldehyde, the stripped solution is treated with ion exchange resins, including at least a cation exchange resin to remove one or more of the metallic ions present, and an anion exchange resin to remove the formate ion, and the acetate ion and silicic acids and silicic acid salts, should they be present in the solution. The deionized butynediol solution then is hydrogenated to form a purified butanediol solution, which is fractionally distilled while maintaining the residue thereof in a fluid state to provide a butanediol product of high quality in high yield.

DESCRIPTION OF THE INVENTION

DESCRIPTION OF THE PREFERRED EMBODIMENTS

Figure 1:
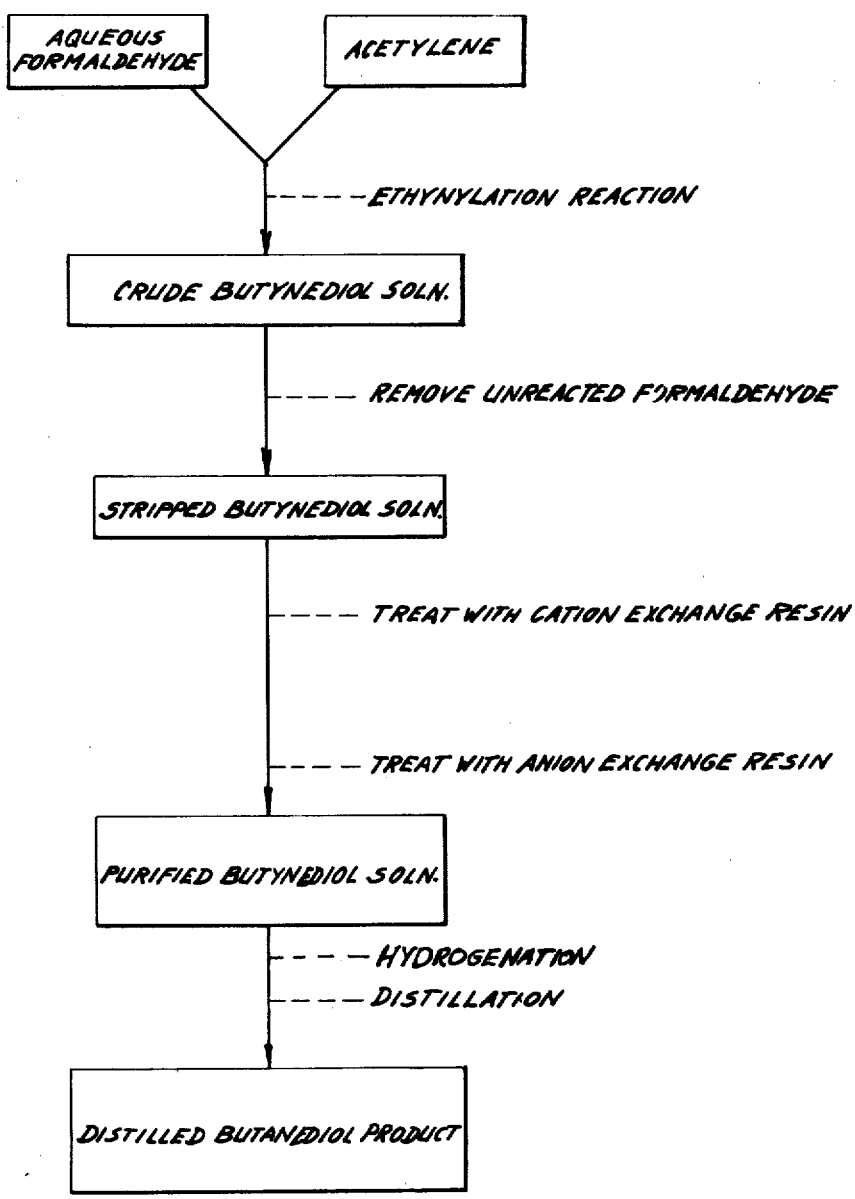
FIG. 1 is a flow sheet of the process of the present invention.

Referring now to FIG. 1, there is shown a flow sheet for carrying out the process of the present invention. The first step in the process is an ethynylation reaction between aqueous formaldehyde and acetylene to produce a crude butynediol solution. Such ethnylation reactions occur in the presence of a suitable catalyst, usually a cuprous acetylide complex, which is supported on an inert carrier, such as magnesium silicate, copper silicate, silica gel, aluminum oxide, activated carbon, diatomaceous earth, and the like. The preferred catalysts of the prior art comprise cuprous acetylide complex on a magnesium silicate carrier, as described in U.S. Pat. No. 3,920,759. However, as mentioned previously, formate ion impurities are formed during the ethynylation process, and acetates are present in the buffered aqueous formaldehyde solution, and metallic ions and silicic acids and silicic acid salts also may be present in the crude butynediol solution upon being leached from the catalyst during the course of the reaction.

The ethynylation reaction, per se, preferably is carried out while stirring the aqueous reaction solution, which is buffered at a pH of 3 to 10, at a temperature of about 60° C.–120° C., and at a pressure of less than 2 atmospheres partial pressure of acetylene, in the presence of an in situ generated catalyst, which is fully described in the aforementioned patent.

The crude butynediol solution from the ethynylation reaction then is heated and/or subjected to reduced pressure to volatilize unreacted formaldehyde, propargyl alcohol by-product, and a portion of the water. It is preferred to strip the solution of formaldehyde to a low level, e.g., 0.1–0.4 weight %, by means of this distillation, before proceeding with ion exchange treatment, which will be described in detail hereinafter, although it may be done after.

Figure 2:
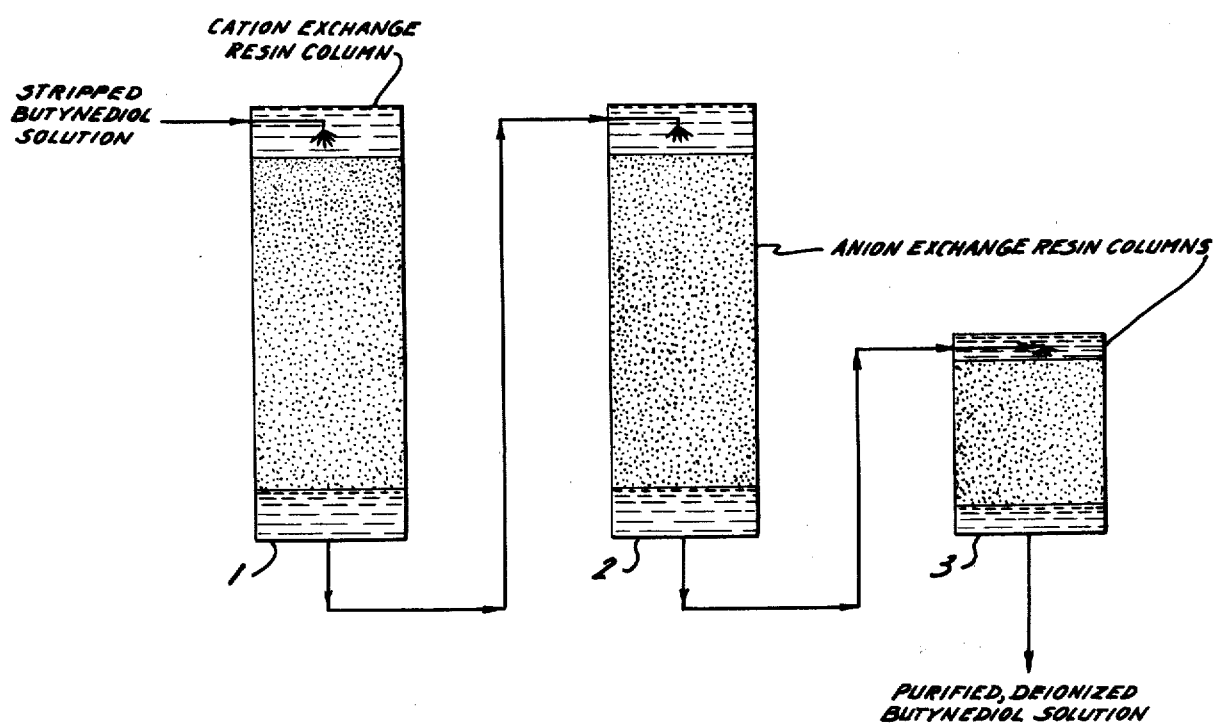
FIG. 2 is a schematic illustration of suitable ion exchange treatment apparatus in accordance with a preferred embodiment of the invention.

At this point in the process, the stripped butynediol solution is treated with ion exchange resins to remove undesired impurities present therein, including at least a metallic ion, usually sodium, magnesium, and/or calcium ion, and formate ion, and acetate ion, if present, and, preferably, silicic acids and silicic acid salts, if they are present, too, in the stripped butynediol solution. As shown in FIG. 2, the ion exchange treatment preferably is carried out in a series of successively connected ion exchange resin beds, each designed to accomplish a specific function with respect to removal of one or more of the unwanted impurities.

The first ion exchange stage is a cation exchange resin, stage 1, which removes metallic ions from the solution. The cation exchange resin is present in its hydrogen form (or free acid form), and is preferably of the strong acid type. Suitable cation exchange resins for use herein include the gel type, synthetic, high capacity resins of the sulfonated polystyrene type, and the porous or macroreticular sulfonic acid type, although other similar resins available in the art may be used as well. A typical cation resin of gel type is Amberlite IR-120, and of the macroreticular type is Amberlite 200, both sold by the Rohm and Haas Co.

The second stage 2 in the ion exchange treatment of the stripped butynediol solution in the preferred embodiment of the invention is an anion exchange resins stage, which removes formate ion, particularly, and acetate ion, if present, from the solution. The anion exchange resin is selected from either the weak or strong base type in their hydroxide or free base form. Both types will remove formate and acetate ions, but the weak base resin is cheaper, and, therefore, is preferred. Suitable weak base resins are the gel type, polyamine and the porous or macroreticular type polyamine resins, which are usually the N, N-dimethylaminomethyl derivatives of polystyrenedivinylbenzene, although others known in the art may be used as well. A typical resin of the gel type of this functionality is Amberlite IRA-47, made by Rohm and Haas Co. A typical porous or macroreticular type is Amberlite IRA-93, also made by Rohm and Haas Co.

If silicic acids and silicic acid salts are present in the stripped butynediol solution, it is preferred to include a small third stage 3, strong base anion exchange resin stage to remove these materials. Removal of these acids and salts has little effect on the yield of distilled butanediol in the process; however, the lifetime of the hydrogenation catalyst used to make butanediol from butynediol is increased considerably when these impurities are removed prior to hydrogenation.

Strong base anion exchange resins suitable for use in the third or second stages are the gel type, synthetic, polyammonium hydroxide resins, and the porous or macroreticular, polyammonium hydroxide derivatives of polystyrenedivinylbenzene resins. A typical resin is Amberlite IRA-400, although others available in the art may be used as well.

The foregoing ion exchange stages and resin beds can be selected and deployed in a number of different ways, individually, or in combination. In each combination the stripped butynediol solution preferably is passed through each bed successively to provide a deionized butynediol solution ready for hydrogenation. A particularly useful combination of stages is a 3-stage system, that is, strong acid type cation resin bed followed by a weak base anion resin bed and a small strong base anion resin bed. In this combination, the cation resin removes both mono and polyvalent cations, and the relatively less expensive weak base anion resin can remove formate and acetate ions from the aqueous stream. The more expensive strong base resin then can remove any silicic acids and silicic acid anions.

Another useful combination is a 2-stage system, namely, a strong acid cation exchange resin bed followed directly by a strong base anion exchange resin bed. This system offers the advantage of requiring one stage less than the preceding combination, but it employs the more expensive strong base resin in the second stage for removal of both strong and weak anions, including silicate anions.

In any particular combination, however, the ion exchange resins need not be contained in separate beds, as shown in FIG. 2, but may be mixed in a special bed, in which they can be separated for regeneration. In general, however, this arrangement is not as efficient as separate beds.

Following the ion exchange treatment, the deionized butynediol solution is catalytically hydrogenated to form a purified butanediol solution. The hydrogenation step is described in detail in the specific examples which follow.

The ion exchange treatment may be carried out after hydrogenation, but is preferably done before hydrogenation, particularly if silicic acids and silicic acid salts, which would reduce the activity and shorten the life of the catalyst, are present.

The purified butanediol solution is then fractionally distilled to produce the desired distilled butanediol product. During the distillation step, first water is removed, then light organic fractions, and finally, pure butanediol is distilled over in high yield.

As a particular feature of this invention, during the distillation, the residue is maintained continually in a fluid state, that is, without gel formation, as occurred during prior art distillations from non-deionized solutions. This difference results from the fact that the gel is composed of metallic salts of formic acid (and acetic acid, if present) and high boiling organic fractions. The deionized butanediol solution of this invention, however, does not contain sufficient metallic ions and formate ion impurities to enable the gel to form. The nondeionized butanediol solutions, of course, have these impurities present in abundance. Since gel traps butanediol liquid therein, the yield of distilled butanediol is increased in the deionizing process of the invention, and its quality is improved. Furthermore, since the liquid residue in this distillation remains fluid throughout, it is not necessary to retain a portion of the butanediol product in it to enable it to flow (for discarding, in a batch process) or to be pumped (for recycling, or disposal, in a continuous process).

The invention now will be described in more detail in the following specific examples, which are not to be considered as limiting but are merely illustrative of the invention. All parts and proportions therein are by weight unless otherwise specified.

EXAMPLE 1

Preparation of Distilled Butanediol by Deionizing Process

A. Preparation of Crude Butynediol Solution

Formaldehyde and acetylene are reacted in an ethynylation process, as described in U.S. Pat. No. 2,920,759, to produce a crude aqueous butynediol solution of 35% concentration. The solution contains as impurities unreacted formaldehyde, magnesium formate, calcium formate, sodium acetate, silicic acids and silicic acid salts.

B. Preparation of Stripped Butynediol Solution

The unreacted formaldehyde in the crude butynediol solution then is removed by distillation to a concentration of 0.1–0.4% of the solution. An analysis for metallic constituents, principally, indicates 100 ppm magnesium, 167 ppm sodium and 135 ppm $SiO_2$. The pH is 5.0 and the conductivity is 930 micromhos.

C. Treatment with Ion Exchange Resins (3-Bed System)

A 3-bed ion exchange resin bed system is constructed in the following manner. The first bed in a glass column 3 inches in internal diameter and 5 feet high, and, it is filled with 0.12 cubic feet of Amberlite IR-120, a strong acid type cation exchange resin, having a capacity of 1.9 meq./ml. (wet) based on the sodium form of the resin.

The second glass column is 6 inches in internal diameter and 4 feet high, and it is filled with 0.32 cubic feet of Amberlite IRA-93, a weak base anion exchange resin, having a capacity of 1.2 meq/ml. (wet). A charge of 0.033 cubic feet of Amberlite IRA-400, a strong base anion exchange resin, having an anion exchange capacity of 1.4 meq/ml. (wet), is placed in a third glass column which is 2 inches in internal diameter and 4 feet high.

Each resin bed is piped up with an inlet and about 4 inches above the resin, and an outlet to the drain to permit regenerant and rinse water to be pumped through each separately. The three resin columns are connected together so that when proper valves are open or closed, liquid can be pumped down through each in turn in the above order.

Each resin bed is rinsed with deionized water and then regenerated. The cation resin bed is regenerated by pumping 17.8 liters of 5% $H_2SO_4$ down through it at a rate of 0.21 liter/minute, and rinsed with 21 liters of deionized water at 0.3 liter/min; the rinse water thereby contains only 49 ppm of $H_2SO_4$. The weak base resin bed is regenerated by pumping 11 liters of 4% NaOH through it at a rate of 0.27 liter/min. followed by rinsing with 24 liters of deionized water at 0.4 liter/min. The final sample of rinse water from the resin bed contained only 40 ppm of NaOH. Similarly, the strong base resin bed is generated with 9 liters of 4% NaOH at 0.2 liter/min., and rinsed with 12 liters of deionized water at the same rate. A sample of the last rinse water from the bed showed only 10 ppm NaOH.

The aqueous butynediol then is pumped through the three beds in series, starting with the cation exchange resin followed by the weak base anion resin and finishing with the strong base anion resin, at a rate of 0.1 liter/min. After the first hour of operation, the deionized butynediol solution is sampled. It contains only 0.01 ppm of magnesium and 2.7 ppm of soluble silicate as $SiO_2$. The pH is 7.8 and the conductivity is 3.1 micromhos. After 51.1 gallons of solution are treated, it contains 0.06 ppm magnesium, 2 ppm sodium, and 3.0 ppm of soluble silicate as $SiO_2$, and the conductivity is 7.9 micromhos.

D. Preparation of Purified Butanediol Solution

The deionized 35% aqueous butynediol then is used as the starting material for the preparation of butanediol by hydrogenation as follows:

A one gallon, stainless steel autoclave, equipped with a removable stainless steel inner liner, hydrogen flow meter and volume integrator, a dispersimax magnetic stirrer, and an automatic temperature controller is used for the hydrogenation runs. The rate and amount of hydrogen feeding to the autoclave is measured accurately both by the pressure drop across an orifice and by the pressure drop in a cylinder of precisely known volume.

The autoclave has a "blow leg" for product discharge which extends to within 0.75 inches of the bottom of the liner. When product is discharged, this leaves a volume of 240 ml. of catalyst and butanediol solution in the bottom of the liner. The liner has two 0.5 by 11.5 inch baffles, one on each side. The reaction temperature is controlled automatically. The signal from the thermocouple actuates the electric heaters of the autoclave and regulates the flow of cooling water in the coils.

For an initial run, the autoclave liner is charged with 72 g. of fresh Raney nickel, and 1581 g. of the deionized butynediol solution. The liner is placed in the autoclave, which is then closed and pressure tested for leaks after replacing the air with nitrogen and the nitrogen hydrogen. The system is considered tight when the total hydrogen loss is less than 0.002 SCFM. The one-liter hydrogen reservoir is pressured to 1800 psig with hydrogen.

The autoclave is then heated to 48° C. without stirring, and the hydrogen pressure is increased to 300 psig. At 48° C., the agitator is started for the start of the hydrogenation. The temperature is leveled off at 50° C. by the temperature controller. The agitation rate is 1435 rpm.

The rate of hydrogen consumption levels off quickly and remains nearly constant during the first half of the hydrogenation. The rate then falls sharply for a few minutes and rises to a new peak rate before it gradually drops to less than 0.002 SCFM at the end. The overall reaction rate in terms of hydrogen consumption is 115 ml. $H_2$ per minute per gram of catalyst. This rate is calculated from the 78 min. reaction time from the beginning to the point when the rate of hydrogen consumption dropped below 0.006 SCFM. The reaction mixture is heated and stirred under hydrogen for an additional two hours beyond this point. The heat is then shut off and the cooling water flow increased. In two hours, the temperature is 25° C. The stirring then is stopped and the catalyst is allowed to settle.

For the next run, another charge of 1580 g. of the butynediol solution is added to the autoclave through a small opening in the top. A slow hydrogen flow through the autoclave keeps air out during the charging procedure. The same procedure is followed as described for the first run. The weight of product recovered in this run is 1585. Fourteen more autoclave runs are made by the same procedure and with the same starting material. The Raney nickel catalyst used in these runs is recovered, washed, and dried. It is analyzed for insoluble silicate salts and has only 0.55% silica as $SiO_2$ compared to 0.43% for fresh Raney nickel. Since this small difference is within the error of the analytical method, it shows that there is no detectable build-up of insoluble silicate salts.

Product from each of the autoclave runs except the first is composited to make a low pressure hydrogenation composite for this series of runs. The composite material then is hydrogenated by the following procedure under more stringent conditions to produce an aqueous butanediol solution.

The same autoclave equipment is used, but it is set for 1500 psig hydrogen pressure. A charge of 1800 g. of the above low pressure hydrogenation composite is added to the empty autoclave together with 72.8 g. of Raney nickel catalyst paste and a little dionized water to rinse the catalyst out of its container. The same hydrogenation procedure is followed except that the reaction temperature is set at 150° C., and the hydrogen pressure is 1500 psig. After a reaction time of 10 hours, the autoclave is cooled, and the catalyst allowed to settle. The product weighing 1705.7 g. then is discharged through the "blow leg", leaving a "heel" of catalyst paste and product in the autoclave. A second high pressure hydrogenation of the same material is made by the same procedure to obtain more butanediol solution for distillation.

E. Preparation of Distilled Butanediol Product

The aqueous butanediol solution then is distilled to provide a purified butanediol product in high yield. In this step, a 1 L., 4-necked distillation flask is equipped with a thermometer, vacuum-tight stirrer, and dropping funnel and is charged with 750 g. of aqueous deionized butanediol. The assembled flask is fitted with a heating mantle, Claisen stillhead, downward condenser, fraction cutter, and receivin flask. Another 250 parts of the butanediol solution is poured into the dropping funnel to be added to the flask later. The flask is stirred and heated, and the water is distilled over at atmospheric pressure as a first fraction. After removal of about one-half of the water, the remaining 250 g. of butanediol solution is added from the dropping funnel and the distillation is continued. When the liquid temperature in the distillation flask reaches 140° C., the heating is stopped.

A clean receiver then is attached, and the distillation system is connected to a pressure regulator, manometer, dry ice cooled trap and vacuum pump. Distillation then is continued at a pressure of 15 mm. of mercury until the pot temperature reaches 110° C. A small liquid fraction (No. 2) then is taken, and after releasing the vacuum with nitrogen, the contents of the trap (manily water) are added to Fraction No. 1. Distillation is continued again at a pressure of 10 mm. of mercury, and a large fraction (No. 3) of anhydrous butanediol is collected up to a pot temperature of 160° C. The receiver is changed thereafter, and a fourth fraction is taken until the pot temperature reaches 200° C. The pressure then is immediately increased with nitrogen to 40 mm. of Hg., stopping the distillation.

During the distillation, the residue in the distillation flask remains very fluid and it continues to remain fluid even as it is cooled down to ambient temperature. No evidence of gel formation is noted at any point in the distillation process.

The butanediol products, the residue, and the other fractions are weighed and analyzed to determine the amount of butanediol produced in relation to the total recovery of organic products and by-products. Fractions 1 and 2 are analyzed by gas chromatography (G.C.) using n-pentanol as an internal standard. Fraction 3, the butanediol product, is analyzed for purity by G.C., and water is determined by Karl Fischer. The freezing point (°C.), carbonyl number, and color (APHA scale) also are measured.

The distillation then is repeated with another sample of the deionized aqueous butanediol and the data for both distillations are presented in Table I below. The data are compared with distilled butanediol prepared by the non-deionizing process of Example 2.

TABLE I
COMPARISION OF BUTANEDIOL PRODUCT QUALITY AND YIELD FOR DEIONIZED AND NON-DEIONIZED PROCESSES

| | Example 1 Deionized Butynediol | | Example 2 Non-Deionized Butynediol | |
|---|---|---|---|---|
| Feed to Hydrogenation Distillation No. | No. 1 | No. 2 | No. 1 | No. 2 |
| DISTILLATION (% OF CHARGE) | | | | |
| Water & Lights | 61.33 | 60.08 | 65.62 | 63.44 |
| Butanediol in Cut 2 (1*) | 0.12 | 0.25 | 0.01 | 0.14 |
| Butanediol (Wt. Cut 3.) | 36.88 | 38.18 | 30.95 | 32.42 |
| High Boilers (Cut 4.) | 0.42 | 0.30 | 0.58 | 0.80 |
| Residue | 0.93 | 0.94 | 2.55 | 2.98 |
| Loss (Difference) | 0.32 | 0.25 | 0.29 | 0.22 |
| DISTILLATION CHARGE | | | | |
| Water (By Distn.) (2*) | 60.46 | 59.26 | 65.34 | 63.08 |
| Butanol, G.C. (3*) | 0.53 | 0.53 | 0.27 | 0.35 |
| Methanol, G.C. (3*) | 0.34 | 0.29 | 0.01 | 0.01 |
| RESIDUE ANALYSIS | | | | |
| Ash, % | | | 19.0 | 19.44 |
| BUTANEDIOL QUALITY | | | | |
| Freeze Point, °C. | 19.6 | 19.6 | 19.1 | 19.0 |
| Carbonyl No. | 0.08 | 0.06 | 0.13 | 0.05 |
| Water, % | 0.10 | 0.07 | 0.23 | 0.21 |
| Butanediol Purity, G.C. (4*) | 99.78 | 99.78 | 99.23 | 99.37 |
| Color (APHA) | 0 | 0 | 0 | 5 |
| HIGH BOILING CUT 4 | | | | |
| Butanediol, %, G.C. | 96.62 | 93.63 | | 68.38 |
| YIELD OF DISTILLED BUTANEDIOL PRODUCT | | | | |
| Butanediol, Cut 3 (5*) | 94.9 | 95.4 | 92.1 | 90.7 |
| Residue (6*) | 2.4 | 2.3 | 5.3 | 5.9 |

NOTES
(1*) A small intermediate cut is taken. The butanediol content is shown and the water content was added to water and lights (No. 1)
(2*) Total water is obtained from the weight of the water & lights by subtracting the methanol and butanol content.
(3*) The butanol and the methanol (weight %) are determined by a careful G.C. analysis of the distillation charge using a known addition of n-pentanol as the internal standard.
(4*) G.C. analysis on an "as is" basis (including water).
(5*) Includes the small amount of butanediol in cuts 1 and 2 as determined by GC (using an internal standard). The yield is parts butanediol per 100 parts butynediol used.
(6*) The organic portion of the residue.

As shown in Table I, an increase in actual yield of butanediol of 3-4% is obtained with the deionized process as compared to the non-deionizing process of Example 2.

EXAMPLE 2

Preparation of Distilled Butanediol by a Non-Deionizing Process

A charge of 18.9 L. of crude 36.5% aqueous butynediol containing 0.5% formaldehyde is added to a 12 gal. open head steel drum. The charge is agitated while the pH is raised to 9.6 by the addition of 58.4 g. of 50% NaOH. The solution is heated with a steam coil to 90° C., and heating and stirring is continued for three hours at 90° C. while another 80.5 g. of 50% NaOH is added to maintain the pH at 8.5 or higher. The thus-treated butynediol solution then is allowed to cool to ambient temperature, and filtered. The pH of the filtered solution then is lowered from 9.5 to 7.5 by the addition of 16.7 g. of 85.9% phosphoric acid. To make up for water lost by evaporation, 2.6 liters of deionized water is added. The formaldehyde content of the butynediol is reduced to essentially zero by this treatment, and the resulting solution contains 35.3% butynediol. The conductivity of the starting materials is 1200 micromhos and that of the treated solution is 3200 micromhos.

Several low pressure (300 psig $H_2$) autoclave hydrogenations are made on the solution by the procedure of Example 1. A composite is made of the product which is recovered from these runs and a portion thereof is hydrogenated in two separate autoclave runs at high pressure (1500 psig $H_2$), also following the procedure of Example 1. The aqueous butanediol solution from the two runs weighs 1743 g. and 1830 g., respectively.

The butanediol solutions then are distilled following the procedure of Example 1 to provide a butanediol product. Gel forms toward the end of each of these two distillations, preventing the recovery of a significant part of the butanediol product. Thereby the weight of the residue increases substantially.

The results are shown in Table I of Example I. The distilled butanediol product prepared by the method of Example 2 is lower in yield and quality, as measured by gas chromotography, than that of Example I. The freezing point, which is also a measure of impurity level, is lower, indicating a higher level of impurities.

EXAMPLE 3

Preparation of Distilled Butanediol Product Using a 2-Bed Ion Exchange System

A total of 0.16 ft.$^3$ of Duolite C-20 cation exchange resin, a strong acid, cation exchange resin of the sulfonated polystyrene type (Diamond Shamrock Co.) is charged to a stainless steel column 5 ft. high by 4 inches in diameter. The resin beads are retained at the bottom on a stainless steel screen of fine mesh size. The steel flanges which closed each end are provided without outlets connected to ¼ inch stainless steel tubing. The entire column is filled with water.

The resin is regenerated from the sodium form to the hydrogen or free acid form by pumping six gallons of 6% hydrochloric acid down through the resin bed at a rate of 0.08 gal/min followed by 15 gallons of deionized water to remove the acid and salt.

A similar column is filled with 0.20 ft.$^3$ of the chloride form of Duolite A-101-D, a strong base anion exchange resin, a polyammonium hydroxide, polystyrene type (Diamond Shamrock Co.). The column is filled with water and the resin is converted to the hydroxide or free base form by pumping 12.7 gallons of 6% aqueous sodium hydroxide solution through it at 0.15 gal/min and at a temperature of 49° C., followed by 20 gallons of deionized water at a rate of 0.2 gal/min. The two columns are connected in series with the cation resin bed first.

A total of 18 gallons of crude 35% aqueous butynediol then is pumped down through the cation exchange resin bed and then down through the anion exchange resin bed at ambient temperature at a rate of 170 ml/min. The butynediol feed contains several metallic constituents, including 150 ppm magnesium and 290 ppm of $SiO_2$ in the form of silicic acids and their salts. The pH is 4.5 and the conductivity 520 micromhos. After passage through the resin beds, the magnesium concentration was 0.04 ppm, the $SiO_2$ was 1.25 ppm., the pH was 7.3, and the conductivity was 4.1 micromhos. This deionized butynediol solution then is used to make butanediol.

The deionized butynediol solution (with 1% formaldehyde added) then is hydrogenated by the two-step hydrogenation procedure of Example 1, and the resulting butanediol solution is distilled as described in Example 1. Two duplicate distillations are made. The butanediol yields are calculated by the method of Example 1 and given in Table 3 below.

TABLE 3

| YIELD AND QUALITY OF DISTILLED BUTANEDIOL PRODUCT | | |
|---|---|---|
| | Distillation No. | |
| | 1st | 2nd |
| Yield Data | | |
| Yield, Fraction Butanediol-3 | 94.6 | 94.1 |
| Yield, Fraction Butanediol-4 (1*) | 2.0 | 2.0 |
| Quality Data | | |
| Freeze Point. °C. | 18.8 | 18.6 |
| Carbonyl Number | 0.04 | 0.05 |
| Water (K.F.), % | 0.15 | 0.17 |
| B$_1$D Purity, G.C. (2*) | 99.77 | 99.81 |
| Color (APHA) | 5 | 0–5 |

(1*) Impure butanediol fraction containing about 80% butanediol.
(2*) % butanediol measured on Fraction 3 materials by gas chomatography. The results are on the "as is" basis (including water as an impurity).

EXAMPLE 4

The Effect of Added Salts on the Recovery of Distilled Butanediol

Formic acid and sodium acetate are added to butanediol prepared from deionized butynediol. The resultant solution then is distilled by the procedure of Example 1 to a pot temperature of 200° C. at 10 mm pressure. The results are compared to a similar distillation of butanediol solution with no added salts. In the case of distillation with added salts, the residue gel forms between 160° C. and 200° C. and contains 6.6 g. of butanediol. With no salts added, the residue of the distillation is very fluid at 200° C., and contains only 0.8 g. of the butanediol.

These results are summarized in Table 4 below.

TABLE 4

| RECOVERY OF BUTANEDIOL BY DISTILLATION | | |
|---|---|---|
| | No Salts | Added Salts |
| Charge for Distillation | | |
| Butanediol, 35% (1*) | 1500 g. | 1500 g. |
| Sodium Acetate | 0 | 1.50 g. |
| Sodium Formate | 0 | 1.95 g. |
| Product Recovery | | |
| Butanediol Fraction | 532.3 g. | 514.9 g. |
| High Boiling Fraction | 7.5 g. | 9.9 g. |
| Residue | 19.4 g. | 28.6 g. |
| Butanediol Found | | |
| Butanediol Fraction | 532.3 g. | 514.9 g. |
| Butanediol in H.B. Fraction | 6.8 g. | 8.9 g. |
| Butanediol in Residue (2*) | 0.8 g. | 6.6 g. |
| Total Butanediol | 539.9 g. | 530.4 g. |

(1*) From two separate autoclave hydrogenations of deionized butynediol.
(2*) Analysis by G.C., using butyrolactone as an internal standard.

I claim:

1. In the process of producing distilled butanediol product from an aqueous butynediol solution which contains metallic and formate ions, which process comprises hydrogenating said butynediol to butanediol and distilling said butanediol, the improvement which is characterized by:
  treating said butynediol solution prior to said hydrogenation treatment with a cationic exchange resin to remove said metallic ion, and an anionic resin to remove formate ion, then hydrogenating and distilling the butanediol at about 160°–200° C. to obtain a distilled butanediol product having a purity of at least 99.7%, in a yield of at least 93%, and a residue which is fluid and pumpable at the distillation temperature for recycling or disposal thereof.

2. A process according to claim 1 wherein said metallic ion is at least one of the group consisting of magnesium, sodium and calcium.

3. A process according to claim 1 wherein said impurities include acetate ion which is removed along with said formate ion.

4. A process according to claim 1 wherein said cation exchange resin is a strong acid type resin.

5. A process according to claim 1 wherein said anion exchange resin is either a weak or a strong base type resin.

6. A process according to claim 1 wherein said butynediol solution is passed successively through a strong acid cation exchange resin bed and a weak base anion exchange resin bed.

7. A process according to claim 1 wherein said butynediol solution is passed successively through a strong acid cation exchange resin bed and a strong base anion exchange resin bed.

8. A process according to claim 7 wherein said resins are contained in a mixed bed.

9. A process according to claim 1 wherein said anion exchange resin includes both weak and strong base type resins.

10. A process according to claim 9 wherein said resins are contained in separate beds.

11. A process according to claim 9 wherein said butynediol solution is passed successively through a strong acid cation and a weak base anion, and a strong base anion exchange resin bed.

12. A process according to claim 1 wherein said strong acid cation exchange resin is a sulfonated polystyrene type resin.

13. A process according to claim 1 wherein said weak anion exchange resin is a tertiary amine polystyrene-divinylbenzene type resin.

14. A process according to claim 9 wherein said strong base anion exchange resin is a polyammonium hydroxide-polystyrene-divinylbenzene type resin.

15. A process according to claim 1 wherein said impurities also includes silicic acids and silicic acid salts, and said anion exchange resin includes at least a strong base resin to remove such impurities.

* * * * *